(12) United States Patent  
Castañeda et al.

(10) Patent No.: US 8,187,309 B2  
(45) Date of Patent: May 29, 2012

(54) SCREW LOCKING SYSTEMS FOR BONE PLATES

(75) Inventors: Javier E. Castañeda, Miami, FL (US); Jorge L. Orbay, Miami, FL (US)

(73) Assignee: Depuy Products, Inc., Warsaw, IN (US)

( * ) Notice: Subject to any disclaimer, the term of this patent is extended or adjusted under 35 U.S.C. 154(b) by 273 days.

(21) Appl. No.: 12/617,059

(22) Filed: Nov. 12, 2009

(65) Prior Publication Data

US 2010/0185246 A1    Jul. 22, 2010

Related U.S. Application Data

(62) Division of application No. 11/017,313, filed on Dec. 20, 2004, now abandoned.

(51) Int. Cl.
*A61B 17/88* (2006.01)
*A61B 17/86* (2006.01)
*A61B 17/56* (2006.01)

(52) U.S. Cl. .......................... 606/305; 606/281; 606/104

(58) Field of Classification Search ................. 606/74, 606/71, 70, 300, 301, 305, 308, 280, 281, 606/286, 291, 104

See application file for complete search history.

(56) References Cited

U.S. PATENT DOCUMENTS

| | | | |
|---|---|---|---|
| 2,329,398 A | 9/1943 | Duffy | |
| 5,275,601 A | 1/1994 | Gogolewski et al. | |
| 5,352,231 A | 10/1994 | Brumfield et al. | |
| 5,496,326 A | 3/1996 | Johnson | |
| 5,536,127 A * | 7/1996 | Pennig | 411/413 |
| 5,601,553 A | 2/1997 | Trebing et al. | |
| 5,643,265 A | 7/1997 | Enrico et al. | |
| 5,681,135 A | 10/1997 | Simonson | |
| 5,709,686 A | 1/1998 | Talos et al. | |
| 5,807,396 A | 9/1998 | Raveh | |
| 6,206,881 B1 * | 3/2001 | Frigg et al. | 606/291 |
| 6,295,773 B1 * | 10/2001 | Alty | 52/202 |
| 6,331,179 B1 * | 12/2001 | Freid et al. | 606/279 |
| 6,436,100 B1 | 8/2002 | Berger | |
| 6,565,573 B1 * | 5/2003 | Ferrante et al. | 606/62 |
| 6,599,290 B2 | 7/2003 | Bailey et al. | |
| 6,623,486 B1 | 9/2003 | Weaver et al. | |
| 6,669,701 B2 | 12/2003 | Steiner et al. | |
| 6,702,817 B2 | 3/2004 | Beger et al. | |
| 6,719,759 B2 | 4/2004 | Wagner et al. | |
| 6,821,278 B2 | 11/2004 | Frigg et al. | |
| 6,955,677 B2 | 10/2005 | Dahners | |
| 7,056,075 B2 * | 6/2006 | Powers et al. | 411/178 |
| 7,179,260 B2 * | 2/2007 | Gerlach et al. | 606/291 |
| 7,285,121 B2 | 10/2007 | Braun et al. | |
| 2002/0058940 A1 | 5/2002 | Frigg et al. | |
| 2004/0122442 A1 | 6/2004 | Lewis | |
| 2004/0172022 A1 | 9/2004 | Landry et al. | |
| 2005/0251137 A1 | 11/2005 | Ball | |

FOREIGN PATENT DOCUMENTS

DE    20203439    7/2003

* cited by examiner

*Primary Examiner* — Pedro Philogene  
(74) *Attorney, Agent, or Firm* — Gordon & Jacobson, PC (57) ABSTRACT

Bone screws have heads which are provided with a hex socket as well as a threaded portion. A screw driver system includes a hex driver and a threaded driver. The screw driver system permits driving the screw through a plate system into a bone until desired compression is obtained. Then the screw is locked to the plate while maintaining the imparted compression.

15 Claims, 6 Drawing Sheets

SCREW LOCKING SYSTEMS FOR BONE PLATES

CROSS REFERENCE TO RELATED APPLICATION

This application is a divisional of U.S. Ser. No. 11/017,313, filed Dec. 20, 2004, now abandoned which is hereby incorporated by reference herein in its entirety.

BACKGROUND OF THE INVENTION

1. Field of the Invention

This invention relates broadly to orthopedic devices. More particularly, this invention relates to systems for locking bone screws relative to bone plates.

2. State of the Art

For various fractures of bones of the body, plating is a well known technique to impart the stabilization desirable for proper healing. In plating, a rigid, typically metal plate is placed on the outer surface of the bone across the fracture, and screws are secured through the plate and into the bone on either side of the fracture in a manner which permits the rigid plate to offer support to the bone during healing.

The screws include threads along a shaft adapted to engage cortical bone. Most commonly, the head portion of the screw is generally a standard screw head which provides a compressive force about a corresponding round screw hole of the plate as the screw is thread into the bone, thereby causing compression of the plate against the bone.

U.S. Pat. No. Re. 28,841 to Allgower describes a plate that is used with generally standard screws having heads with a convex undersurface. The plate includes oblong screw holes which each define at one end an upper ramped portion and a generally smaller radius of curvature about the ramped portion. In use, a hole is drilled into the bone through the screw hole adjacent the ramp and a screw is inserted through the screw hole adjacent the ramp into the drilled hole and rotated until the head of the screw contacts the ramp. Upon such engagement, there is displacement of the bone plate in a direction to move the ramped portion away from the screw and the cause the plate to apply pressure to maintain the bone parts together about the fracture in tight engagement.

More recently, particularly at the metaphysis of long bones though not limited thereto, there have been desirable results with screws having exteriorly threaded heads which threadably engage threads in the plate to lock the screws relative to the plate and thereby limit compression of the plate relative to the bone. However, such systems do not provide the necessary control of compression between the plate and bone. Control over compressive forces is lost as soon as the threads of the head of the screw lock relative to the plate. Therefore, such a system provides sub-optimal stability.

Certain plates sold by Synthes are designed with a hole called a COMBI-HOLE™. The COMBI-HOLE™ is an elongated screw hole including two joined circular sections, each extending through approximately 250°. One of the circular sections is threaded and thus adapted to received a screw with a threaded head at a fixed angle. When used as such, the system has the same lack of control over compression as discussed above.

SUMMARY OF THE INVENTION

It is therefore an object of the invention to provide a plate and screw system whereby the amount of compression between the plate and bone can be controlled completely by the surgeon.

It is an additional object of the invention to provide a plate and screw system which permits complete control over compression prior to and during locking the screw to the plate.

In accord with these objects, which will be discussed in detail below, bone screws according to the invention have heads which are provided with a hex socket as well as a threaded portion. A screw driver system according to the invention includes a hex driver and a threaded driver. The threaded driver is provided with an axial through bore which is dimensioned to receive the hex driver. The screw driver system is coupled to a screw by threadably engaging the threaded driver with the threaded portion of the screw head, and delivering the hex driver through the bore in the threaded driver to engage the hex socket in the screw head. Optionally, a set screw is used to secure the hex driver to the threaded driver. The end of the threaded driver is dimensioned to have a diameter larger than the diameter of the head of the screw with which it is used. According to a first embodiment, the screw head is frustroconical with a smooth side surface and the screw head includes internal threads coaxial with the hex socket. The first embodiment is used with a bone plate having a frustroconical screw hole.

When the screw is attached to the driver system and is passed through the hole in the bone plate, the threaded driver alone is used (or both drivers coupled together are used) to rotate the screw to engage the bone. After the screw is advanced into the bone, the frustroconical screw head enters the frustroconical screw hole in the bone plate, but is prevented by the threaded driver from contacting the inner wall of the screw hole. The larger diameter end of the threaded driver prevents the screw head from advancing further. Moreover, the end of the threaded driver contacts the area of the bone plate surrounding the screw hole and exerts compression on the plate as the screw is further advanced into the bone. When the desired compression is reached, turning of the threaded driver is stopped (and if the drivers where engaged, they are now disengaged) and the hex driver is used to further advance the screw. Turning the hex driver while holding the threaded driver advances the screw while starting to decouple the threaded portion of the screw head from the threaded driver. In order to maintain compression until the screw head is locked in the screw hole of the bone plate, the length of the threads on the screw head and the threaded driver prevent the screw head from being decoupled before the screw head is locked. When the frustroconical screw head lockingly engages the frustroconical screw hole, the threaded driver is backed off the screw head by turning it in the direction opposite to driving.

A second embodiment of a bone screw according to the invention is identical to the first embodiment but has a threaded exterior surface on the wall of the frustroconical head. The threaded surface creates high localized pressure between the thread crests and the tapered screw hole wall of the plate. It also causes some scoring and a better mechanical hold.

A third embodiment of a bone screw has a cylindrical head with two unequal diameter circumferential edges, one near the top and one near the bottom of the head, that make simultaneous contact with the tapered screw hole wall of the plate when the head is locked to the plate.

A fourth embodiment of a bone screw has a cylindrical head with external threads and an internal hex socket. This embodiment of the screw is used with the second embodiment of the threaded driver which has internal threads which engage the exterior of the screw head and is also used with a bone plate that has a cylindrical threaded screw hole. The threads on the head of the screw preferably advance at a similar rate to the threads on the shaft so as to maintain the compression achieved while the head is being locked to the plate. Alternatively, the pitch of the screw head threads may be decreased slightly with respect to the screw shaft threads so as to increase compression slightly as the screw is locked to the plate.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
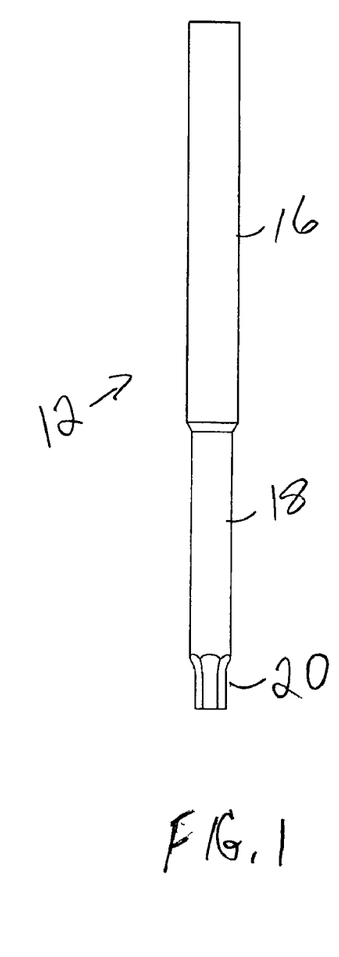
FIG. 1 is a side elevational view of a hex screw driver according to the invention.
Figure 2:
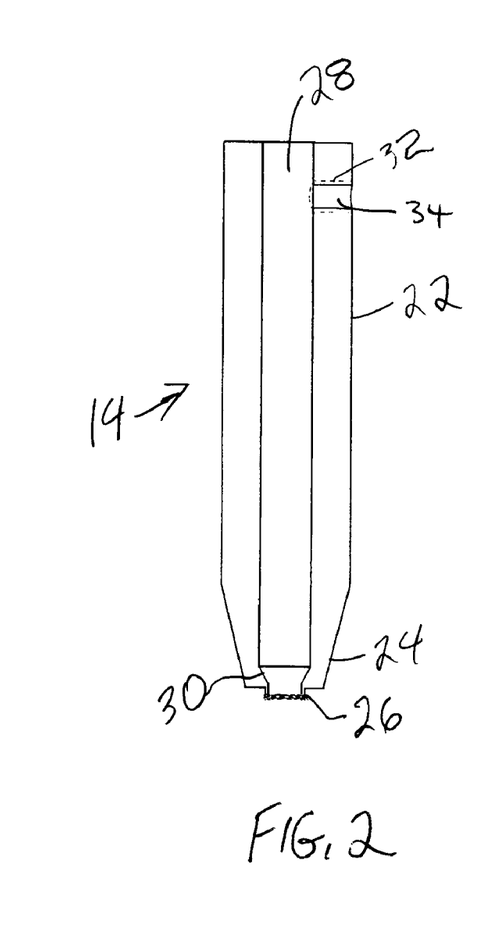
FIG. 2 is a transparent side elevational view of a threaded screw driver according to the invention.
Figure 3:
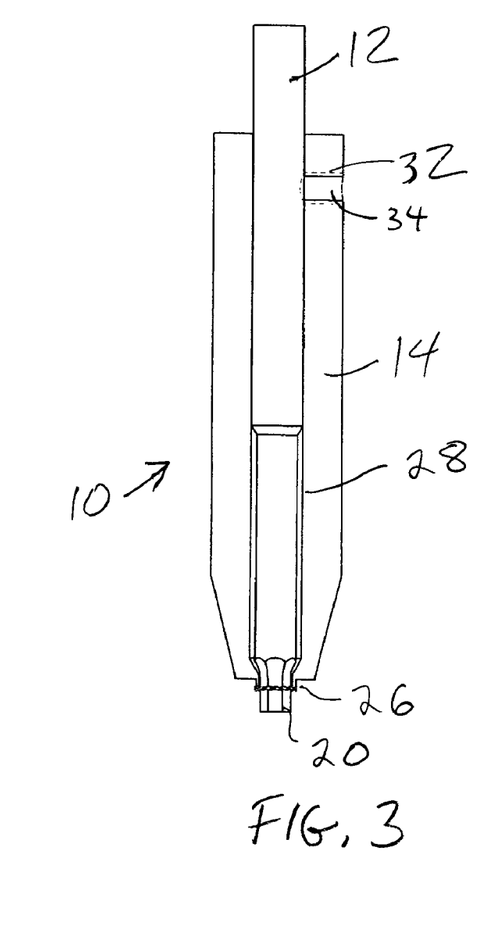
FIG. 3 is a transparent side elevational view of the hex screw driver coaxially inserted through the threaded screw driver.

Turning now to FIGS. 1-3 a first embodiment of a screw driver system 10 according to the invention includes a hex driver 12 and a threaded driver 14. The hex driver 12 includes a cylindrical handle 16, a smaller diameter shank 18, and a male hex end 20. The threaded driver 14 includes a cylindrical handle 22 with a tapered end 24. An exteriorly threaded cylinder 26 extends from the tapered end 24. An axial through bore 28 extends through the handle 22 and through the cylinder 26. The through bore 28 exhibits a tapered wall 30 just prior to the cylinder 26. Optionally, a set screw hole 32 is arranged orthogonal to the bore 28. The hex driver 12 is dimensioned to fit through the bore 28 as shown in FIG. 3 with the male hex end 20 extending beyond the threaded cylinder 26. The tapered wall 30 in the bore 28 prevents the hex driver 12 from passing through the bore. The screw driver system 10 is designed for use with a bone screw of the type shown in FIG. 4.

Figure 4:
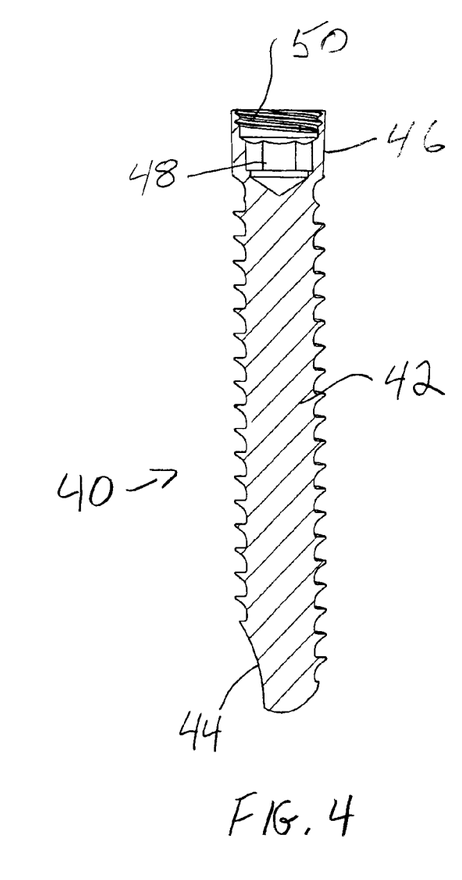
FIG. 4 is a longitudinal sectional view of a first embodiment of a bone screw according to the invention.
Figure 5:
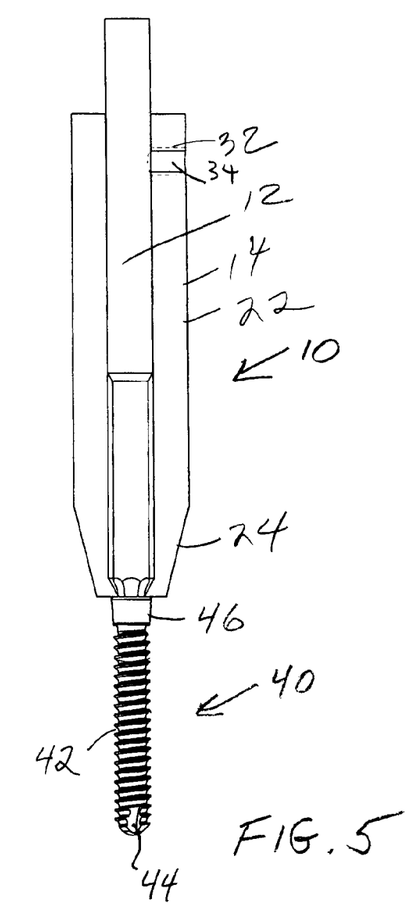
FIG. 5 is a partially transparent side elevational view of the screw drivers of FIGS. 1 and 2 coupled to the screw of FIG. 4.

Turning now to FIG. 4, a bone screw 40 includes a threaded shaft 42 having a cutting flute 44 at one end and a screw head 46 at the other end. The head 46 is substantially frustroconical and houses a hex socket 48 and a threaded inner wall 50 which is coaxial with the hex socket. Referring now to FIGS. 3-5, those skilled in the art will appreciate that, when assembled, the threaded cylinder 26 of the driver 14 engages the threaded inner wall 50 of the screw head 46 and the male hex end 20 of the driver 12 engages the hex socket 48. The screw and driver assembly is shown in FIG. 5. When the screw and drivers are assembled as shown, the screw is ready to be inserted through a bone plate and threaded into bone.

Figure 6:
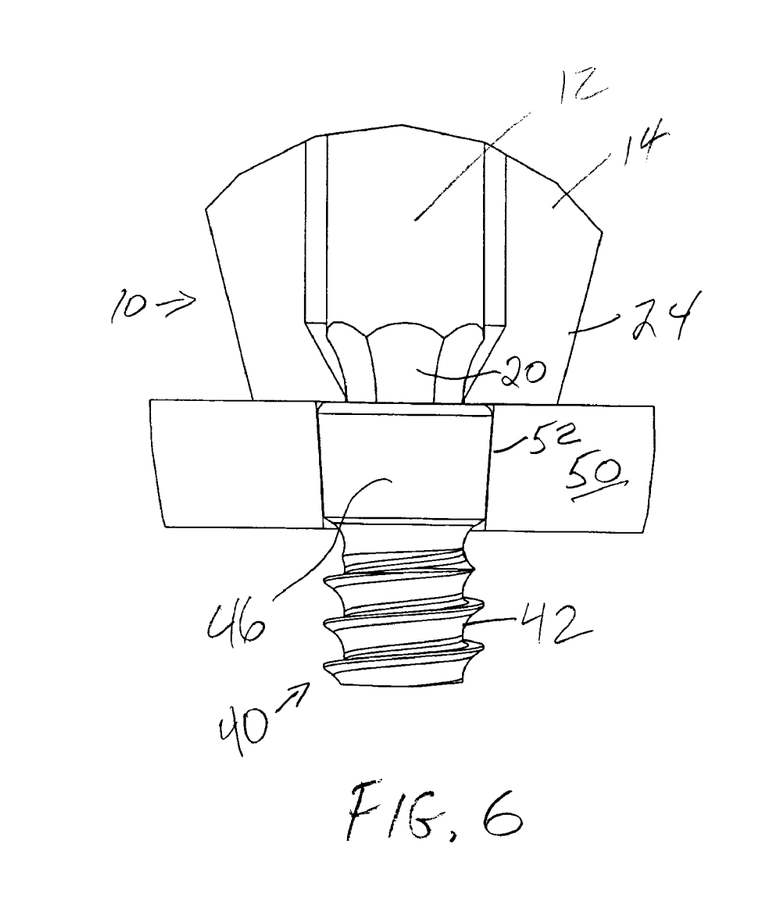
FIG. 6 is a broken partially transparent side elevational view of the screw drivers and screw of FIGS. 1-5 and a bone plate showing the screw unlocked from the plate during plate compression.
Figure 7:
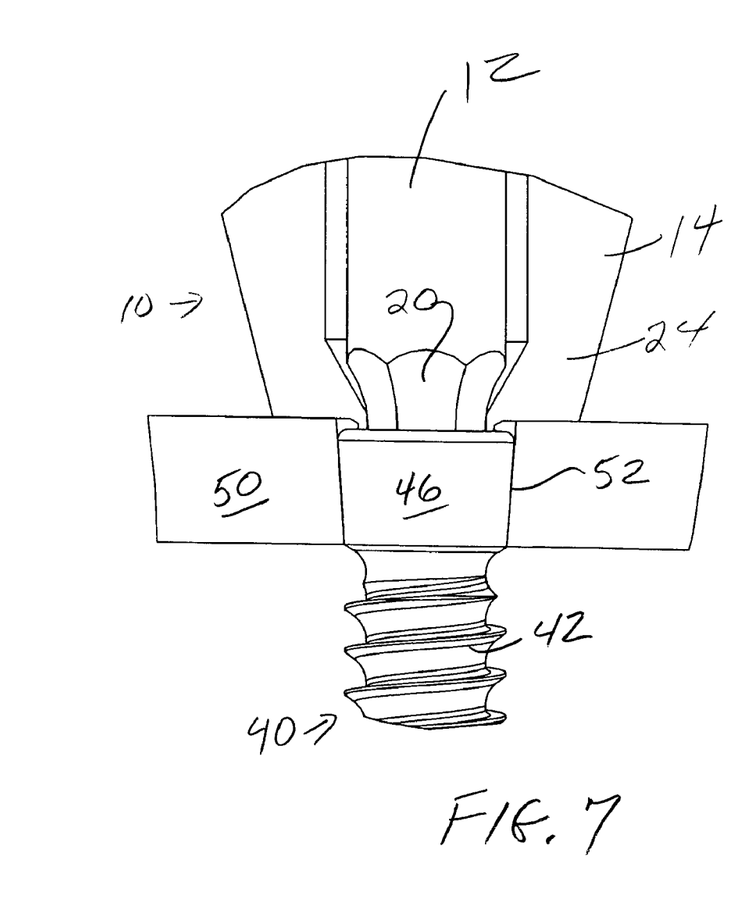
FIG. 7 is a view similar to FIG. 6 but showing the screw locked to the plate.

FIGS. 6 and 7 show two stages of applying the screw 40 to a bone plate 50 having a frustroconical screw hole 52. After the screw and drivers are assembled as shown in FIG. 5 and the drivers are optionally fastened to each other with a set screw 34 through the set screw hole 32, the handle 22 of the driver 14 is turned while the screw 40 is inserted through the plate 50 and into a pre-drilled hole in the bone (not shown). As the screw advances into the bone, the head 46 of the screw advances toward the plate 50 and ultimately enters the frustroconical hole 52 as shown in FIG. 6. Before the head 46 can frictionally engage the hole 53, the tapered end 24 of the driver 14 abuts the plate 50. Since the head 46 of the screw 40 is threadably coupled to the end of the driver 14, it is prevented from advancing away from the driver 14 into the hole 52. When the screw, driver and plate are arranged as shown in FIG. 6, rotating the driver 14 advances the screw into the bone while the tapered end 24 of the driver 14 compresses the plate 50 against the bone. When the surgeon feels that the proper amount of compression has been achieved, rotation of the driver 14 is stopped. If necessary, the set screw is 34 released from the hole 32 (FIG. 5) and the hex driver 12 is rotated further in the same direction while the threaded driver 14 is held stationary. This causes the screw 40 to advance while the head 46 rotates out of engagement with the driver 14 until the head 46 frictionally engages the hole 52 as shown in FIG. 7. The driver 12 may then be removed by lifting it out of the socket in the screw head and the bore in the driver 14. The driver 14, if not decoupled from the screw by the advancement, can then be uncoupled by reverse rotation.

From the foregoing, those skilled in the art will appreciate that the system of the invention allows the surgeon to carefully apply a controlled amount of compression to the plate prior to locking the screw to the plate. It also maintains the selected compression while the screw is being locked to the plate. The tapered end of the threaded driver serves two functions, it reduces friction between the driver and the plate, making it easier to rotate the driver under compression. It also provides a clearer view of the screw and screw hole during insertion of the screw into the hole. However, it is not necessary that the driver be tapered.

Figure 8:
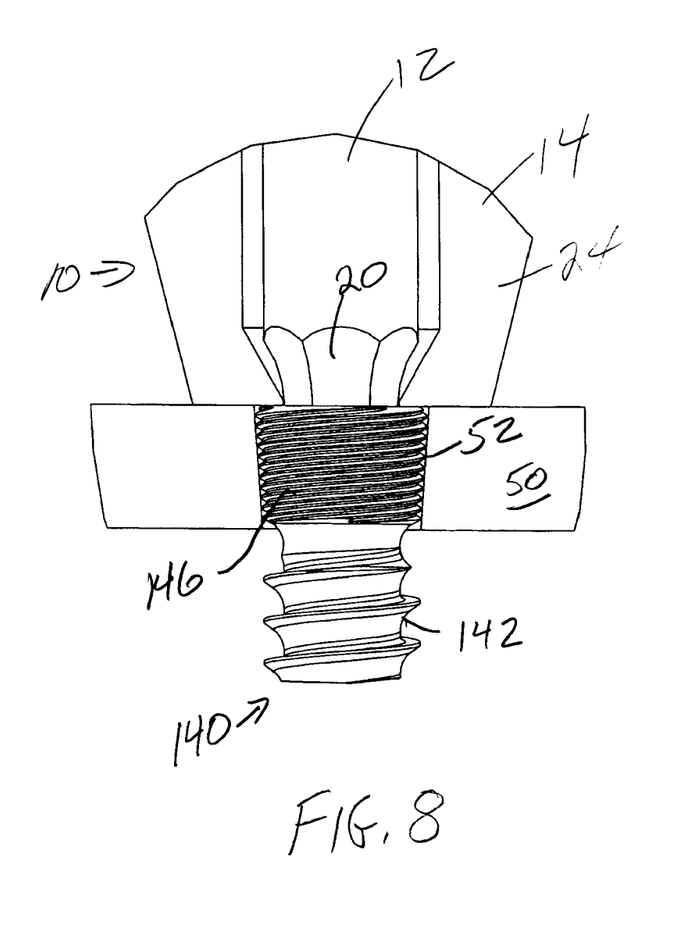
FIG. 8 is a view similar to FIG. 6 but showing a second embodiment of a screw according to the invention.
Figure 9:
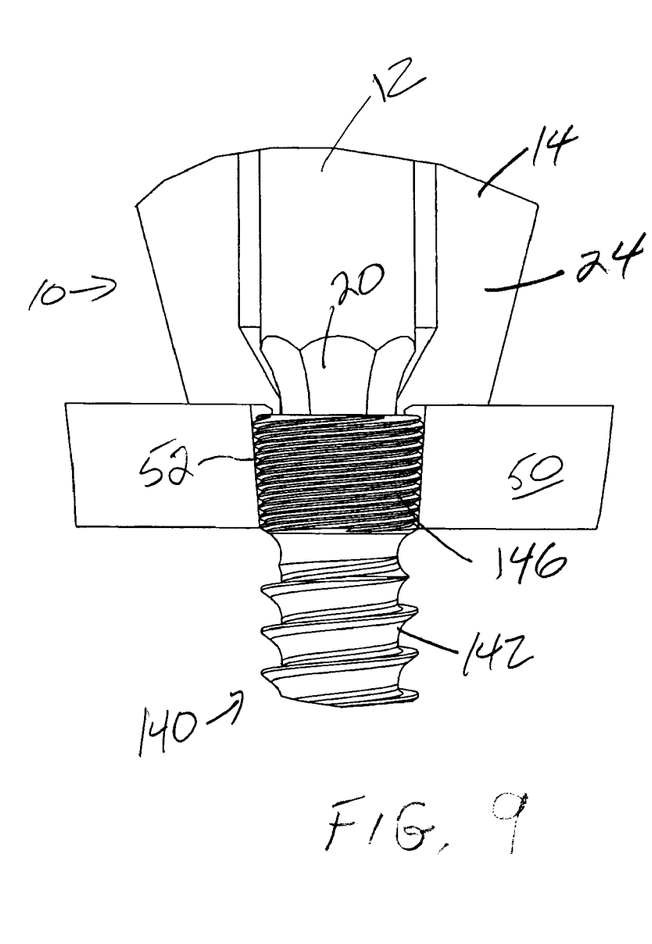
FIG. 9 is a view similar to FIG. 7 but showing the second embodiment of the screw.

FIGS. 8 and 9 illustrate an alternate embodiment of a screw 140 which is substantially identical to the screw 40 having a threaded shaft 142, a cutting flute at one end (not shown) and a frustroconical head 146 at the other end. The difference between this screw 140 and the screw 40 is that the outer surface of the head 146 is threaded. The screw 140 works with the same driver assembly 10 and bone plate 50 as the screw 40 in the same manner as described above but the threaded surface 146 creates high localized pressure between the thread crests and the tapered screw hole wall 52 of the plate. It also causes some scoring and a better mechanical hold. The pitch of the threads 146 should be the same as the pitch of the threads 142 to help maintain the same level of compression and create one scoring track.

Figure 10:
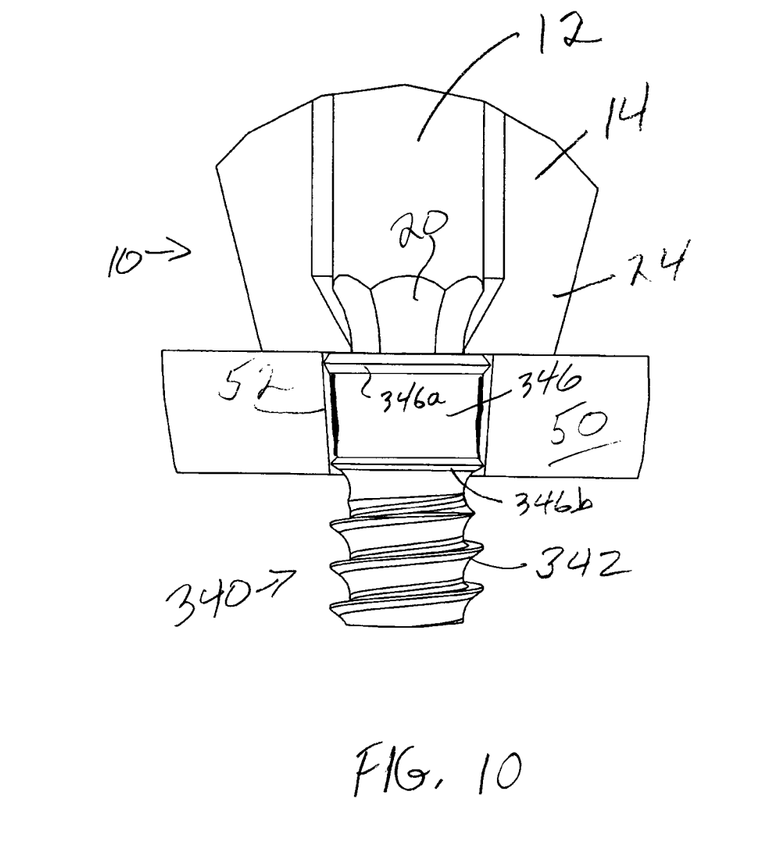
FIG. 10 is a view similar to FIG. 8 but showing a second embodiment of a threaded screw driver according to the invention and a bone plate having a threaded screw hole.
Figure 11:
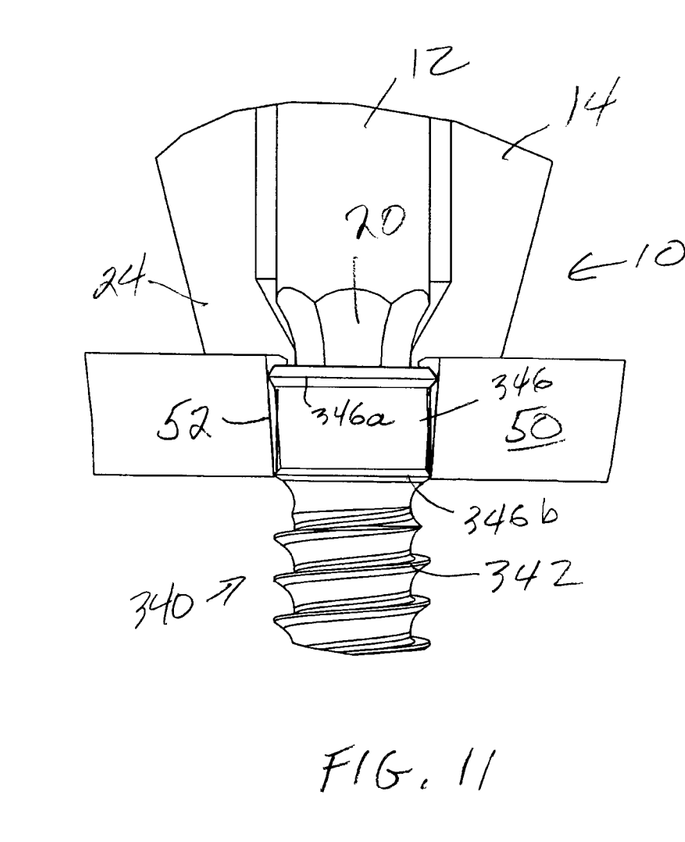
FIG. 11 is a view similar to FIG. 9 but showing the second embodiment of a threaded screw driver and the bone plate having a threaded screw hole.
Figure 13:
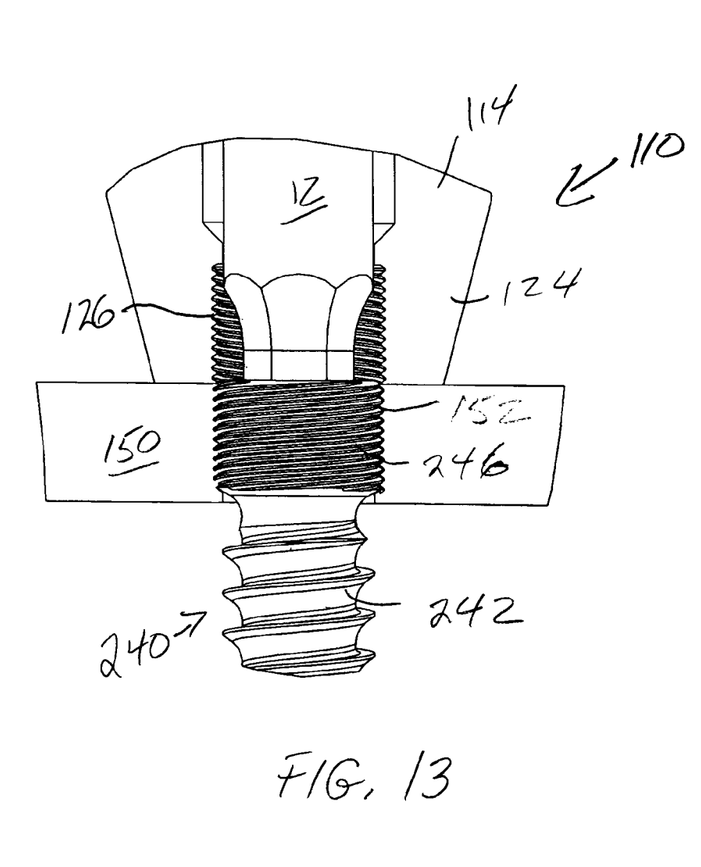
FIG. 13 is a view similar to FIG. 9 but showing another embodiment of a bone screw according to the invention.

FIGS. 10 and 11 illustrate another embodiment of a bone screw according to the invention. The screw 340 has a threaded shaft 342 and a cylindrical head 346 with two unequal diameter circumferential edges 346a, 346b. The interior of the head 346 is the same as the head 46 of the screw 40 (FIG. 4) and the screw is used with the driver assembly 10 (FIG. 3) and the bone plate 50 described above. When the screw 340 is locked into the tapered hole 52 as shown in FIG. 13, the two circumferential edges 346a, 346b make simultaneous contact with the tapered hole, one near the top and one near the bottom. Such circumferential ridges can also be used on screws with frustroconical heads or any shaped head which will rotate within the screw hole.

Figure 12:
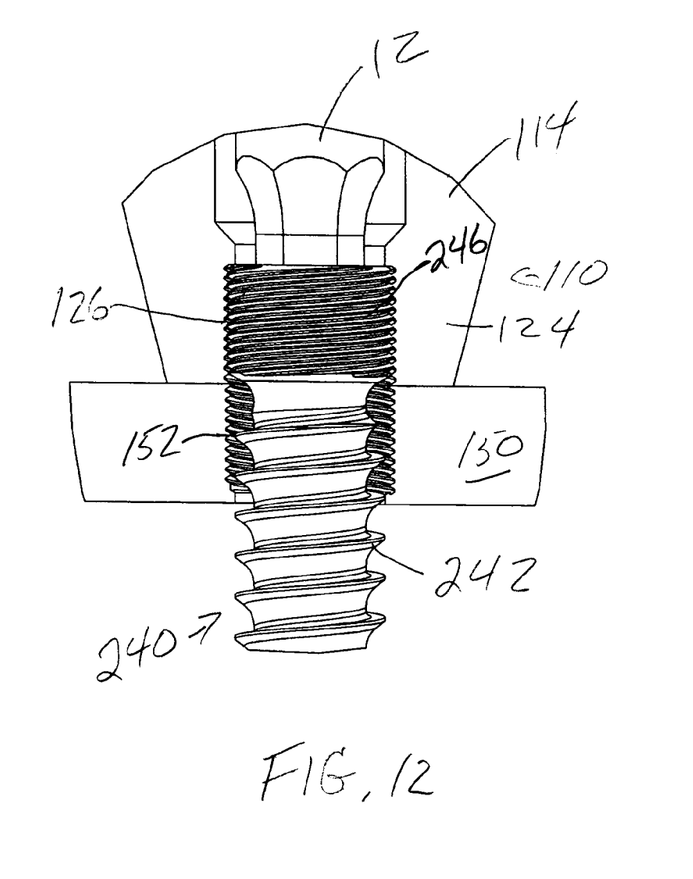
FIG. 12 is a view similar to FIG. 8 but showing another embodiment of a bone screw according to the invention.

FIGS. 12 and 13 illustrate another embodiment of a bone screw 240, a second embodiment of a bone plate 150, and a second embodiment of a driver system 110. The driver system 110 uses the same hex driver 12 as the driver system 10 but uses a different threaded driver 114. The driver 114 has an interiorly threaded cylindrical recess inside its tapered end 124 as opposed to the exteriorly threaded cylinder 26 of the driver 14 (FIGS. 2 and 3). The screw 240 has a cylindrical head 246 which is provided with threads that match the threads in the recess 126 of the driver 114. The screw head 246 also has an interior hex socket like the hex socket 48 in the screw 40 (FIG. 4) but it does not have interior threads like the threads 50 in the screw 40. The threads on the shank 242 of the screw 240 have generally the same pitch as the threads on the head 246. The plate 150 has a screw hole 152 with interior threads which match the threads of the screw head 126. As can be seen in FIGS. 10 and 11, the threads 152 terminate before reaching the bottom of the plate 150. The screw, driver, and plate of this arrangement operate in a manner similar to the systems described above. The screw 240 is attached to the driver 114 by threading its head 246 into the threaded recess 126 of the driver. The driver 114 drives the screw into the bone and advances the head 246 to the top of the plate 150, but prevents it from entering the threaded hole 152. The tapered end 124 of the driver abuts the top of the plate and compresses it. When the surgeon feels the appropriate amount of compression, the hex driver 12 is rotated while keeping the threaded driver 114 stationary. This rotates the screw head 246 out of engagement with the threaded recess 126 and into engagement with the threaded hole 152. The screw head bottoms out on the threads in the hole 152 before passing through the plate 150. It is desirable that multiple thread starts be provided on the screw head 246 to avoid compression when the plate threads start to engage and to avoid cross-threading. It is important to note that the external threads on the head 246 are free to engage both the driver and the plate and are not blocked from engaging either by any other part of the head.

There have been described and illustrated herein embodiments of a bone plating system and methods of using the same. While particular embodiments of the invention have been described, it is not intended that the invention be limited thereto, as it is intended that the invention be as broad in scope as the art will allow and that the specification be read likewise. For example, while the screws have been described as having a hex socket which is driven by a hex driver, it will be appreciated that other types of sockets and drivers can obtain substantially the same results as a hex socket and driver. It will therefore be appreciated by those skilled in the art that yet other modifications could be made to the provided invention without deviating from its scope as claimed.

What is claimed is:
1. A method for attaching a plate to a bone with a screw through a hole in the plate, said method comprising:
attaching the screw to a driver;
inserting the screw through the hole in the plate;
driving the screw into a bone while biasing the plate against the bone with the driver but not the screw; and
releasing the screw from the driver while locking it to the plate.

2. A bone plating system for stabilizing bone, comprising:
a bone screw having,
a threaded shank having a first end, a second end, and an overall diameter; and
a screw head having a portion of larger diameter than said overall diameter, said screw head defining a threaded first driver engagement means for engaging a first driver for the screw and a non-threaded second driver engagement means for engaging a second driver for the screw,
said threaded first driver engagement means located radially outward of said non-threaded second driver engagement means;
a screw driver system having,
a first driver having an elongate body having a first end and a second end with a throughbore extending through said body from said first end to said second end and having first screw engagement means located at said second end for engaging said threaded first driver engagement means, and
a second driver having an elongate body having a first end and a second end and dimensioned to fit through said throughbore of said first driver, and having said second screw engagement means located at said second end of said second driver for engaging said second driver engagement means; and
a bone plate having,
at least one screw hole adapted to receive said screw and lockingly engage said screw head, said first screw engagement means having a diameter exceeding a diameter of said at least one screw hole,
wherein said second driver is adapted to rotate said bone screw into bone with compression developed between said threaded shank of said bone screw and said second end of said first driver, and once sufficient compression is developed, said first driver is adapted to rotate said screw head of said bone screw into engagement with said at least one screw hole in said bone plate.

3. The system according to claim 2, wherein:
said first driver engagement means includes threads located inside said screw head.
4. The system according to claim 3, wherein:
said second driver engagement means includes a socket portion of said screw head.
5. The system according to claim 2, wherein:
said screw hole is tapered.
6. The system according to claim 2, wherein:
said plate has a top and a bottom and said screw hole is threaded from said top to a location between said top and bottom.
7. The system according to claim 2, wherein:
said first and second drivers are releasably lockable to each other.
8. The system according to claim 2, wherein:
said first screw engagement means is threads and said second screw engagement means is a hex driver.
9. The system according to claim 8, wherein:
said threads are internal to said first driver.
10. The system according to claim 8, wherein:
said threads are external to said first driver.
11. The system according to claim 2, wherein:
said bone plate comprises metal.

12. The system according to claim 2, wherein:
said screw head is frustoconical along an exterior surface that axially extends coextensively with said first and second driver engagement means.

13. The system according to claim 2, wherein:
said screw head is cylindrical.

14. The system according to claim 13, wherein:
said screw head includes an exterior having a length, and said screw includes helical threads abut an entirety of said length of said exterior.

15. The system according to claim 2, wherein:
said screw head has a pair of external axially spaced apart non-helical circumferential ridges structured for engagement with the inner surface of the screw hole in the bone plate,
wherein upon insertion of the screw head into the screw hole said circumferential ridges provide engagement with said screw hole.

* * * * *